US 11,359,660 B2

United States Patent
Juszczyk et al.

(10) Patent No.: US 11,359,660 B2
(45) Date of Patent: Jun. 14, 2022

(54) CONNECTION ARRANGEMENT OF TWO COMPONENTS

(71) Applicant: CeramTec GmbH, Plochingen (DE)

(72) Inventors: Mateusz Maria Juszczyk, Velden (DE); Anne Gebert De Uhlenbrock, Weißenohe (DE)

(73) Assignee: CERAMTEC GMBH, Plochingen (DE)

( * ) Notice: Subject to any disclaimer, the term of this patent is extended or adjusted under 35 U.S.C. 154(b) by 0 days.

(21) Appl. No.: 17/012,406

(22) Filed: Sep. 4, 2020

(65) Prior Publication Data

US 2021/0071697 A1 Mar. 11, 2021

(30) Foreign Application Priority Data

Sep. 6, 2019 (EP) .................................... 19195938

(51) Int. Cl.
| | | |
|---|---|---|
| *F16B 11/00* | (2006.01) | |
| *F16B 17/00* | (2006.01) | |
| *F16B 7/02* | (2006.01) | |
| *A61F 2/30* | (2006.01) | |

(52) U.S. Cl.
CPC ............ *F16B 11/002* (2013.01); *F16B 7/025* (2013.01); *F16B 17/00* (2013.01); *A61F 2/30* (2013.01); *Y10T 403/4966* (2015.01)

(58) Field of Classification Search
CPC ....................... A61F 2/30; A61F 2/3609; A61F 2002/30072; A61F 2002/30474; A61F 2002/3006; A61F 2002/365; A61F 2002/3654; F16B 11/002; F16B 17/00; Y10T 403/49; Y10T 403/4949; Y10T 403/4966; Y10T 403/4991

USPC ................................. 403/274, 280, 282, 285
See application file for complete search history.

(56) References Cited

U.S. PATENT DOCUMENTS

| | | | | | |
|---|---|---|---|---|---|
| 5,181,929 | A | * | 1/1993 | Prats | ...................... A61F 2/3609 623/22.43 |
| 5,405,394 | A | * | 4/1995 | Davidson | ............... A61F 2/3609 623/18.11 |
| 5,549,703 | A | * | 8/1996 | Daigle | .................. A61F 2/3609 623/22.43 |
| 5,871,547 | A | * | 2/1999 | Abouaf | .................. A61F 2/3609 623/22.15 |

(Continued)

FOREIGN PATENT DOCUMENTS

| | | |
|---|---|---|
| DE | 4405447 A1 | 8/1995 |
| WO | 2017/114521 A1 | 7/2017 |

OTHER PUBLICATIONS

European Search Report for EP 19195938.6, dated Apr. 23, 2020.

*Primary Examiner* — Josh Skroupa
(74) *Attorney, Agent, or Firm* — Fitch, Even, Tabin & Flannery, LLP (57) ABSTRACT

A connection arrangement (4, 4') of two components (1, 2) according to the invention has a curved surface portion having a contact point on at least one of these components. The curved surface portion can extend over the entire surface of a groove, for example. The other component has a taper. When assembling the two components before a force is applied, a line connection is created from the 2-contact point connection and when force is applied, the line connection changes through plastic deformation into a strip connection, on the basis of which the two components (1, 2) hold together.

8 Claims, 9 Drawing Sheets

(56) References Cited

U.S. PATENT DOCUMENTS

| | | | | |
|---|---|---|---|---|
| 8,753,405 B2 * | 6/2014 | Kennedy | ............... | A61F 2/3609 |
| | | | | 623/22.42 |
| 8,974,540 B2 * | 3/2015 | Podolsky | .............. | A61F 2/3609 |
| | | | | 623/22.4 |
| 10,136,933 B2 * | 11/2018 | Meulink | ............... | A61F 2/3609 |
| 2014/0121713 A1 | 5/2014 | Meulink | | |

* cited by examiner

CONNECTION ARRANGEMENT OF TWO COMPONENTS

CROSS-REFERENCE TO RELATED APPLICATION

This application claims priority from European Patent Application No. EP 19195938.6, filed Sep. 6, 2019, which is hereby incorporated herein by reference in its entirety for all purposes.

The invention relates to an arrangement for connecting two components in an orthopedic system. An attachment of a first orthopedic component is securely connected to a recess, for example in the form of a groove, a bore in a second orthopedic component. The connection arrangement can be formed as a form-fitting, non-positive, or frictional connection arrangement or a combination thereof. The attachment of the first orthopedic component can be formed in the form of a truncated cone. The groove of the second orthopedic component can have an arched, convex surface. The joining of two components is facilitated by the presence of an arched surface on one component. The components are self-aligned or aligned relative to one another. Damage is avoided. When connecting the first to the second orthopedic component, an orthopedic system is created that has a secure linear connection between two components.

The prior art comprises various disclosures of connecting means between two parts.

It is known to connect two parts to one another in a form-fitting manner by means of a conical connection. Such a connection, a morse taper or machine taper, is the standardized form of a tool taper for clamping tools, e.g. large drills, reamers, and chucks in the tool holder of a machine tool. The torque is transmitted from the hollow taper of the driven tool spindle to the clamping shaft of the tool in a frictional manner by static friction as a result of the self-locking. The angle of inclination of the morse taper is about 1° 26' to about 1° 30' relative to the longitudinal axis. A secure conical connection by means of static friction requires the required longitudinal expansion of the connection.

Matching taper connections are used in a plurality of orthopedic devices. For example, modular femoral implants can use a morse taper, possibly with a different angle of inclination, to attach the proximal end of a shaft to a ball head. In the case of modular femoral implants, the distal shaft can comprise a frustoconical proximal end, which has the male part of the connection, wherein a recess of the part to be connected to the shaft has a suitable inner cone shape.

For example, US 2014/0121713 discloses a system for connecting orthopedic components, wherein a projection of a first component is inserted into an orifice of a second component. The projection of the first component is divided into various regions, wherein the periphery of the projection of the first component has deformable surface elements. The cross section of the regions has a straight tapered profile. In a special embodiment it is disclosed that the cross section of the projection has a taper towards the outside.

The secure, positionally precise connection of two orthopedic components by means of a taper connection requires a corresponding longitudinal expansion of the connection region. This required length is not available in various applications, for example in the region of the shoulder joint. Therefore, only taper connections having a small longitudinal expansion can be used there. Despite the greatest care during implantation, there is a risk that the connecting elements will not be inserted orthogonally relative to their longitudinal axes, but tilted. This can result in damage to the components and restricted mobility of the joint. This often causes inflammation of the tissue surrounding the region of the implant, which in turn can be associated with possible pain.

Starting from this, the object of the invention is to ensure a secure, permanent, detachable and positionally precise arrangement for connecting two orthopedic components.

According to the invention, this object is achieved by a connection arrangement having the features of claim 1.

Because the contact surface is curved, a connection arrangement is created, in which the contact tensions in the region of the contact surfaces are reduced in a very soft manner and there is therefore no gradual drop in the contact tension, as would be the case with a sharp line connection, wherein, when assembling the first and the second component, before a force is introduced, a line connection is created from a 2-contact point connection, and when the force is applied the line connection changes into a strip connection by plastic deformation, on the basis of which the two components hold together.

This is explained below by way of example, which is also shown in the drawings and described in the associated description. However, the invention is not limited to this preferred example. In this example, the connection arrangement consists of a conical attachment or projection of a first component which is inserted into a groove of a second component. The groove has a convex curved surface. When assembling the two components, the conical attachment or projection of the first component is inserted into the groove of the second component. See in particular FIG. 10. At an angle that deviates from 90°, a 2-contact point connection is created first and during the further insertion a line connection of the two components is created. This line connection runs on or around the conical attachment or projection or also on the convex curved surface and forms a closed circumferential line connection. This applies before force is applied. If a force is subsequently applied, for example by a blow to one of the components in its connecting direction, the line connection changes into a strip connection by means of plastic deformation, on the basis of which the two components hold together. If a line connection remained after the force was applied, there would be a gradual drop in the contact tension at the (sharp) line connection. Such tension jumps easily break one of the components, which must be avoided in an orthopedic system. According to the invention, however, after the introduction of force, the line connection has become a strip connection by plastic deformation. As a result, the contact tensions are reduced in a soft manner. In this context, "in a soft manner" means that there is no sharp or abrupt change in the contact tension, but rather a soft or gentle change over a specific region. There is thus no gradual drop, i.e. no abrupt drop in contact tension. When using the connection arrangement, i.e. when using the orthopedic system, a further introduction of force may or will result, which widens the strip connection by further plastic deformation. This creates a self-adjusting connection arrangement that responds in a self-regulating manner to high force inputs. One of the components preferably consists of a metal. It is also sufficient if only the contact surface of this component is made of metal. Titanium, for example, is a metal that is ideally suited for orthopedic systems. The other component or its contact surface preferably consists of a ceramic. Ceramic is much harder than a metal, so that the plastic deformation will take place in the metal.

A substantial feature of the invention is the line connection of the two components, which is transformed into a strip connection when force is applied. In extreme cases, it is also possible to connect the two components without first creating a 2-contact point connection, but immediately creating a line connection. For this purpose, the first component would have to be inserted into the groove of the second component, absolutely precisely at an angle of 90°. Even a very slight deviation from this 90° would first create a 2-contact point connection. See in particular FIG. 10. The angle is shown there. This has already been explained above. It is a theoretical approach that, when connecting two components, first a line connection and then a strip connection is created without the line connection being preceded by a 2-contact point connection, wherein in practice, especially during an operation, it is very unlikely that this will occur. Regardless of this, assembling the two components without first establishing a 2-contact point connection would make use of the present invention.

The width of the strip connection is preferably between 0.5 mm and 2 mm and depends on the size of the force application and thus on the degree of plastic deformation.

An orthopedic system has at least two components and a connection arrangement according to the invention.

The invention relates to an orthopedic system which comprises an arrangement for connecting two components. An attachment, formed in the form of a tongue or a projection, of a first component is securely connected to a recess in the form of a groove of a second component. The connection can be formed as form-fitting, non-positive, or frictional connection, or a combination thereof. The attachment formed at a first end of a first component can be in the form of a truncated cone, the diameter of which increases from the distal end. The increase in diameter can be a constant increase. The attachment can also have a shape deviating from a truncated cone, for example a cylindrical shape, having a constant diameter. The periphery of the attachment can have different dimensions, depending on the shape and the position. The entire surface of the attachment or portions or partial regions thereof are part of the connection arrangement and form a connection means between a first and a second component. In the mounted, assembled state of two components, the surface or partial regions of this first component is in an operative connection to a surface or partial regions of this second component. According to the invention, the operative connection is created along a linear contact, a circumferential line.

In another embodiment, the attachment can include at least two regions. These regions can be arranged separately, at a distance from one another. The cross section of the first region, which is arranged at the distal end of the first component, is smaller than the diameter of the cross section of the second region, which is arranged spaced apart from the distal end. The two regions can be formed conically. The angle of the taper of the first region can deviate from the angle of the taper of the second region. It can be bigger or smaller. The two angles of the tapers can also have the same values. The first region can be formed as an insertion aid and facilitate the implantation of the component. The second region can serve as part of the connection arrangement and ensure the fixed, secure positioning of the component. For this purpose, the second region of the attachment has the surface regions by means of which the operative connection can be established.

The groove, formed at a second end of the second orthopedic component, is delimited by a peripheral surface and a base surface. The peripheral surface can be formed as an arched, curved surface. Starting from the distal end of the groove, the cross section of the groove can decrease over a first region until the smallest cross section is reached. This smallest cross section, the apex, can be approximately half the depth of the groove. From the apex, the cross section can increase to the bottom of the groove or can remain constant. Thereby, the curvature, a convex surface of the recess of the groove, of the second component is created. The groove of an embodiment according to this description has a curvature and an apex. The apex can be arranged at any distance from the base surface of the groove.

Embodiments are also possible, the curvature of which has a plurality of apexes and therefore the surface of the groove is formed in the shape of a wave.

The peripheral surface, the surface of the groove, can follow various mathematical functions. For example, it can be formed by a polynomial or a sine function or another mathematical function and comprise only one or more apexes. According to the invention, it is also possible for the curve shape to be formed by a combination of a plurality of mathematical functions. The curve shape can be continuous, wherein the function thereof can be continuously differentiated twice at any point. The curvature of the surface can extend over the entire peripheral surface or only over partial regions thereof. According to the invention, the portion of the peripheral surface which is formed by the curvature can comprise a single vertex. This curved portion can extend over the entire peripheral surface or only over a partial region of the peripheral surface.

According to the invention, the curved surface, as described above, can also be formed on the projection or the attachment of the first orthopedic component. Starting from the distal end of the projection, the cross section of the projection can increase over a first region until the largest cross section, the apex, is reached. This can be approximately half the length of the projection. From the largest cross section of the projection, the apex, the cross-section can decrease to the proximal end of the projection. Thereby, a convex surface of the projection is created. With regard to the curvature, the positioning, and the expansion in the longitudinal direction of the curvature which forms the surface of the projection, the above applies. If the curved surface is formed on the projection of the first component, the second component has, for example, a cylindrical or conical groove, a recess.

Depending on the application, the degree of curvature and the position of the apex on the recess or the projection can vary.

The diameters of the recess of the second component and of the projection of the first component are coordinated with one another in such a way that a permanent, secure connection is created when joining them, regardless of on which component the curved surface is formed. The curved surface supports the orthogonal alignment of the two components. After the correct assembly, a linear contact is always created between the two components, wherein the linear contact with respect to the projection or the recess is closed, i.e. forming a circle which surrounds the projection or circles the recess. The linear contact preferably extends in one plane, but can also deviate therefrom.

If, when joining the two components, they are aligned at an angle to one another that deviates from an orthogonal alignment, the two components can first touch at two points. This two-point contact is converted into a linear contact with the application of an appropriate force. Thereby, a secure connection between the two components is generated.

According to the invention, one of two components has a curved surface in the region in which the two components are joined together. The curved surface comprises 50%, preferably 30%, particularly preferably 15%, but at least 10% of the entire area on which the curved surface is arranged. In other words, the curved surface is part of the peripheral surface of a groove, for example, the above information relates to the peripheral surface of this groove. A particular embodiment of a connection arrangement according to the invention comprises a single curved surface. This curvature consists of an ascent, an apex, and a descent, for example half of a sine period. Surprisingly, it was found that a single curved surface is sufficient to provide a secure connection between two components.

If two components are to be permanently but detachably connected to an orthopedic system by means of an adapter, the connection arrangement according to the invention can be arranged between the adapter and the first component and/or between the adapter and the second component. Both the adapter and the components can have a curved surface. It is also possible for the adapter to have two curved surfaces. A connection between the adapter and the first component is established by means of a first curved surface and the connection between the adapter and the second component is established by means of a second curved surface. An orthopedic system having at least three components and at least two connection arrangements is created according to the invention.

An advantage of the invention is that the contact point of the two components is precisely defined. It can be calculated precisely before the two components are assembled and always remains constant both after correct installation and under heavy loads. Thus, the stress distribution or the stress distribution pattern remains constant, which is not the case with standard taper connections. In addition, jamming is avoided, especially with a large ratio of diameter to height of the connection.

Another advantage of the invention is that two components automatically align themselves orthogonally during the course, i.e. during the installation process. In addition, damage can be avoided by a connection arrangement according to the invention during the installation process. Due to the increase in the diameter of a recess following the apex of the recess of a second component, the distal end, or an edge at the distal end of a first component, cannot damage the recess of the second component after the two-point contact has been made. There is enough free space to avoid damage after centering the two components. In this context, "centering" means the manual application or insertion of a frustoconical first component into a recess of a second component, or vice versa. This is one of the first steps when joining two components; a two-point contact is created. In this process stage, an orthogonal alignment of the two components to one another is not required or guaranteed.

A connection arrangement of two components according to the invention has a curved surface portion having a contact point on at least one of these components. The curved surface portion can extend over the entire surface of a groove, for example.

The other component has a taper. When assembling the two components before a force is applied, a line connection is created from the 2-contact point connection and when force is applied, the line connection changes through plastic deformation into a strip connection, on the basis of which the two components hold together.

LIST OF REFERENCE SIGNS

| | |
|---|---|
| 1 | First orthopedic component |
| 2 | Second orthopedic component |
| 4, 4' | Connection arrangement |
| 5 | Attachment, projection |
| 6 | Distal end of 5 |
| 7 | First end of 1 |
| 8 | Adapter |
| 9 | Groove of 8 |
| 10 | Groove of 2 |
| 11 | Second end of 2 |
| 12 | Bottom, base surface of 10 |
| 14 | Opening of 10 |
| 16 | Peripheral surface, surface |
| 17 | Shaft |
| 18 | Ball head |
| 19 | Location |
| 20 | Flat side |
| 21 | Surface portion |
| 22 | Surface portion |
| 23 | Curved surface portion |
| 26 | Outer peripheral surface of 8 |
| 27 | Contact surface |
| 28 | Peripheral surface, surface |
| 29 | Contact surface |
| 30 | Curved surface portion |
| 31 | End of 30 |
| 32 | Hollow cylinder |
| 33 | Longitudinal axis |
| 34 | Ring or torus |
| 35 | Taper |
| 36 | Contact points |
| 37 | Longitudinal axis |
| 38 | Gap |
| T | Depth of 10 |
| D1 | Diameter |
| D2 | Diameter of 2 |
| Q | Cross section |
| K | Apex |
| KP | Contact point |
| H | Height |
| HN | Height of groove base KP |
| M | Intersection point of 16 with the opening of 10 |
| A | Intersection point of 16 with 1 |
| R | Radius of 16 |
| α | Angle |
| B | Angle |
| X | Distance |
| Y | Central axis |
| Z | Section from FIG. 6 |
| AB | Gap from KP to K |
| Y | Central axis |

The invention will be explained with reference to the drawings, in which.

All figures contain partial, schematic representations of the invention and are used by way of example to explain the invention. Special embodiments of the invention can deviate from these figures.

Figure 1:
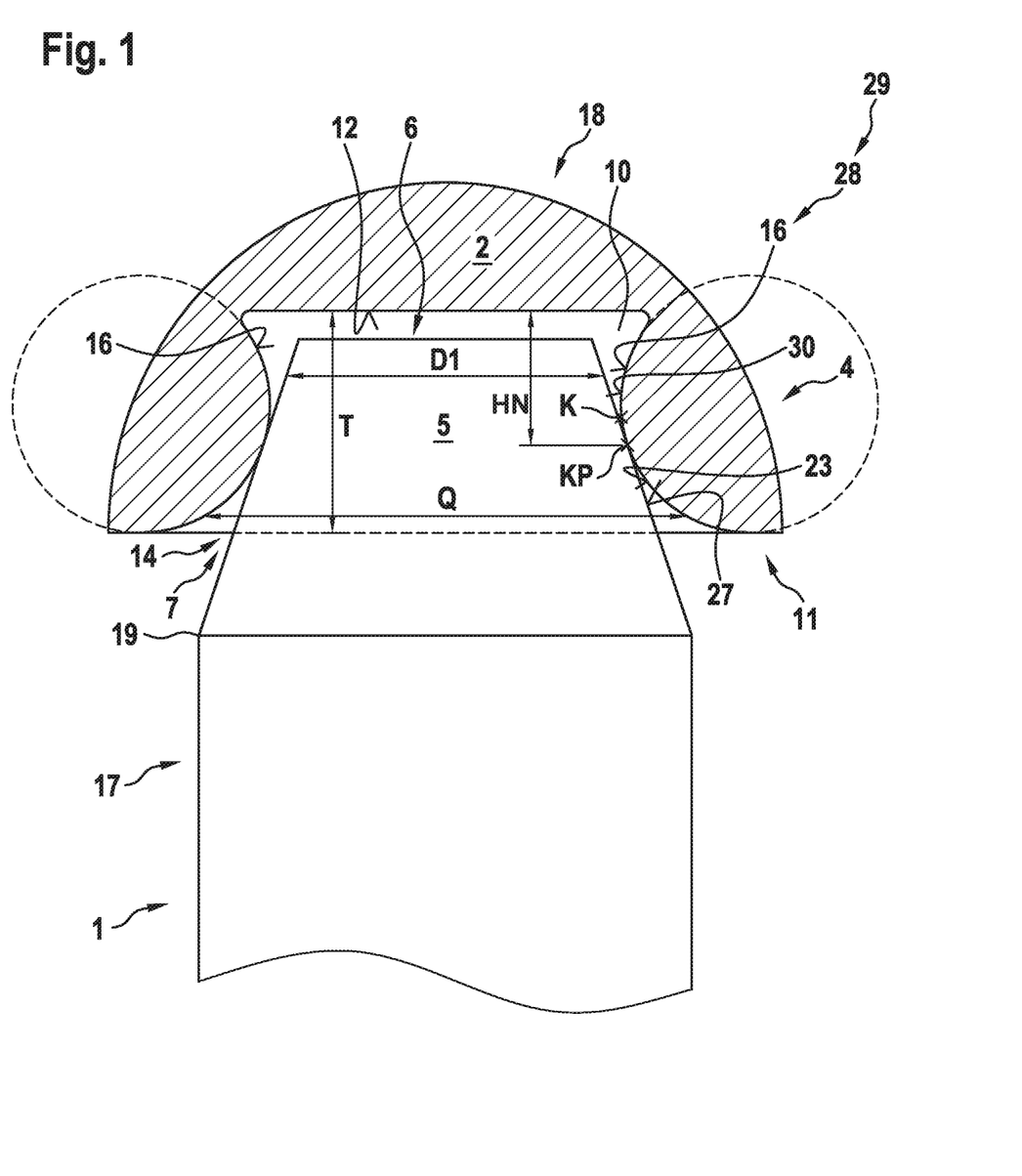
FIG. 1: is a cross section of the connection between two components, in sections, partially in section and in a schematic representation.

FIG. 1 shows the connection arrangement 4 of two orthopedic components, here a shaft 17 of a first component 1 with a ball head 18 of a second component 2. The region of the shaft 17 shown in FIG. 1 has a projection or attachment 5 at its first end 7. Starting from a location 19 of the shaft 17, the diameter D1 of the attachment 5 decreases continuously up to its distal end 6. In the embodiment according to FIG. 1, the attachment 5 is formed in the form of a truncated cone. The truncated cone has a peripheral or contact surface 27. The two components can be part of a hip joint prosthesis, a shoulder joint prosthesis or a finger or ankle prosthesis or other joint prostheses.

The second component 2 has a recess or groove 10. The groove 10 is delimited by a peripheral surface 16 and a base surface or a bottom 12 and opposite the bottom by an opening 14. The peripheral surface 16 can be formed entirely or partially as a contact surface 29. The contact surface 29 can be formed in a portion or a region of the peripheral surface 16. Starting from the second end 11 of the component 2, from the opening 14 of the groove 10, the peripheral surface 16 of the groove 10 is wholly or partially curved. The curvature creates a convexly curved surface 28 which is identical to the contact surface 29 and in FIG. 1 identical to the peripheral surface 16. Starting from the opening 14 of the groove 10, the amount of the diameter or the cross section Q of the groove 10 decreases to a point, the apex K. From this apex K, the amount of the cross section Q increases again until the region in which the peripheral surface 16 merges into the base surface 12 of the groove 10. Thereby, a curved surface 28 of the groove 10 is created, which comprises a surface portion 23 which is formed as an ascent, an apex K, and a surface portion 30 which is designed as a descent.

When joining the shaft 17 of the first component 1 with the ball head 18 of the second component 2, a contact between the two components is created at a contact point KP. In this embodiment of the invention, the contact point KP lies on the peripheral surface 16 or the contact surface 27 below the apex K in the direction of the second end 11 or the opening 14. The gap between the contact point KP and the base surface 12 of the groove 10 is designated in FIG. 1 by the reference sign HN. The gap AB (see FIG. 7) of the contact point KP from the apex K depends on the type of truncated cone of the first component and the curvature of the contact surface 27.

The contact between the two components is thus in this embodiment below the apex K in the direction of the orifice. The contact point KP at which the operative connection takes place is arranged at a distance from the apex K on the contact surface 27, in the direction of the opening of the second component 2. Only if the truncated cone is not one according to the invention, but a cylinder, for example, does the contact point and apex coincide. In the case of a truncated cone or taper having a very large angle, the contact point is close to the orifice of the groove 10.

The contact surface 27 of the component 1 and the contact surface 29 of the component 2 are in operative connection. Through the inventive design of the curved contact surface 29 or surface 28 of the groove 10 and the contact surface 27 of the shaft 17, the contact point of the two components can be precisely determined and fixed. This is particularly the case if the contact surface 27 forms a mathematical function, such as a circle or a parabola in cross section. A circle is particularly easy to calculate the position of the contact point KP. This is of great advantage in the case of components which, owing to their application, can have only a small length in the longitudinal direction. A secure connection of the two components can be achieved despite the shallow depth T of the groove 10. Orthopedic systems having secure connections between two components can be provided in the region of shoulder joints or for small children, or in the veterinary sector.

Figure 2:
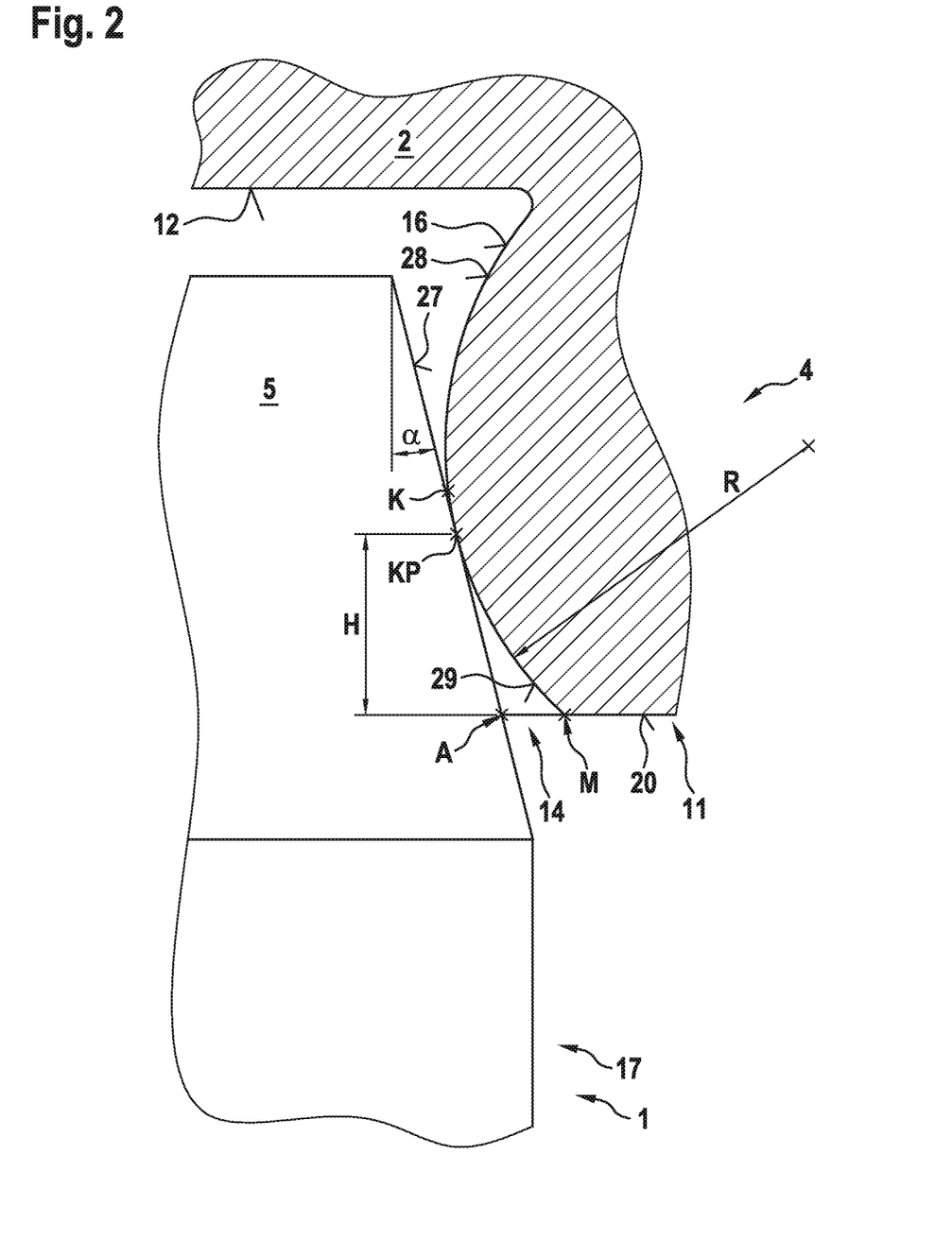
FIG. 2 shows the connection point enlarged according to FIG. 1, in section, and in a schematic representation.

FIG. 2 shows the connection arrangement 4 of two components in an enlarged representation. It can be seen that the contact of the first component 1 with the second component 2 concentrates on a narrow contact region. A line contact is created between the contact surface 29 and the contact surface 27, at the contact point KP.

The line contact is determined by the radius R of the contact surface 29 or the surface 28 of the component 2 and the angle α of the contact surface 27 of the component 1. The position of the contact point KP can be determined by appropriate changes. With a constant radius R and a smaller amount of the angle α, the contact point KP moves away from the opening of the second end 11 of the second component 2 to the apex K at which the diameter of the groove 10 is the smallest. The amount of H, the height at which the contact point KP is arranged away from the opening 14, increases. If, on the other hand, the angle α increases with the same radius R, the distance H of the contact point KP from the opening 14 is reduced accordingly.

In the embodiment according to FIG. 2, the curved contact surface 29 or surface 28 at location M merges into the second end 11 of component 2. This second end 11 is formed as a flat side 20. An intersection point M is created between the contact surface 29 of the groove 10 and the flat side 20. The intersection point M is the point that also defines the end of the curvature of the contact surface 29 in the direction of the second end 11 of the groove 10. After joining the components 1 and 2, the intersection point M and a point A on the contact surface 27 on the shaft 17 of the first component 1 are arranged spaced apart from one another. The point A lies at the intersection point M in a horizontal extension of the flat side 20 in the direction of the shaft 17 on the first component 1. A connection arrangement 4 according to the invention has a distance between the intersection point M and the point A, which decreases in the direction of the contact point KP until the amount of the distance at the contact point KP is 0.

In the embodiment according to FIGS. 1 and 2, the peripheral surface 16 corresponds to the contact surface 29 and the surface 28.

Figure 3:
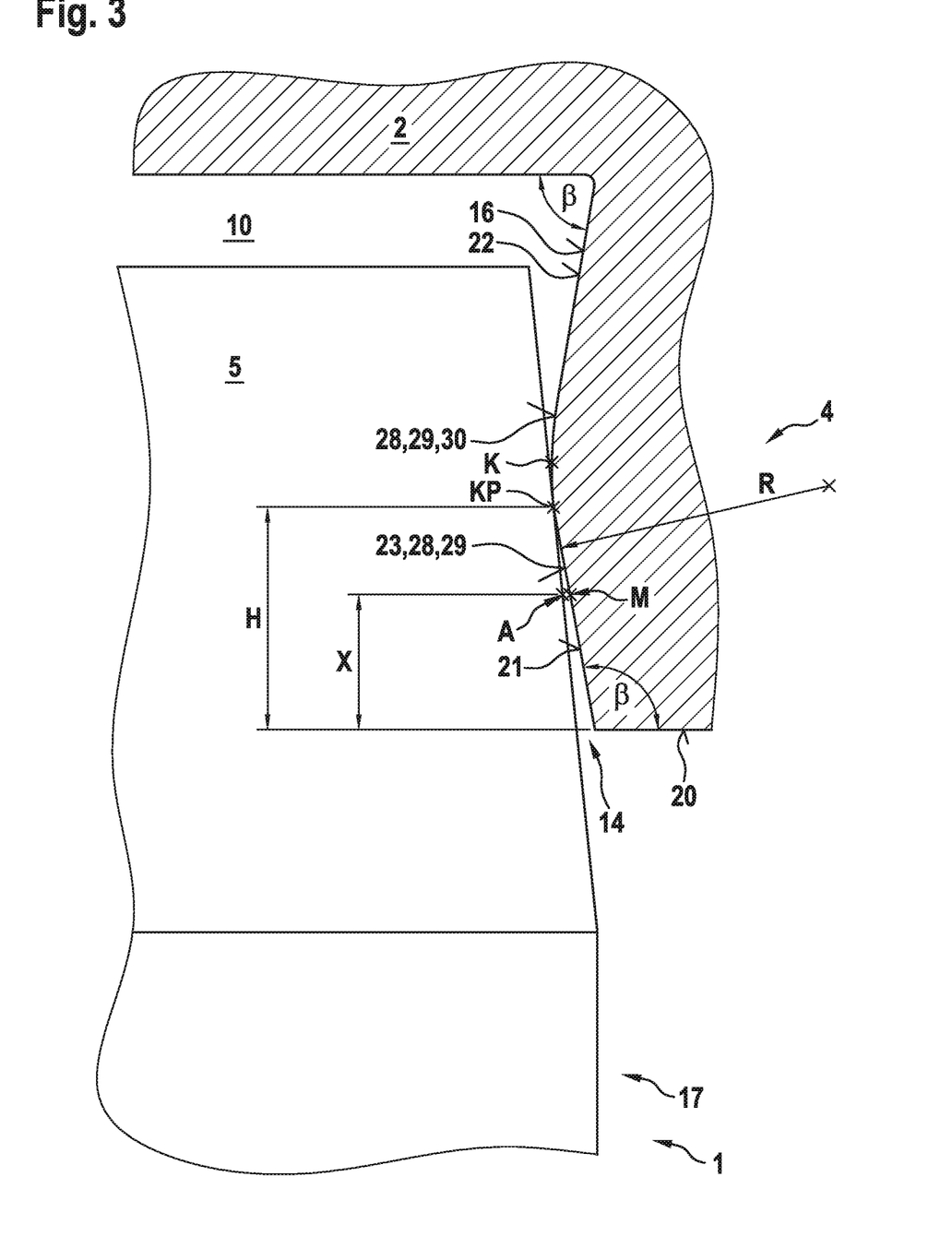
FIG. 3 is an alternative embodiment of the connection point in section and in a schematic representation.

FIG. 3 shows an alternative embodiment of a connection 4 according to the invention of two orthopedic components 1 and 2. The peripheral surface 16 of the groove 10 comprises a plurality of portions or regions. The peripheral surface 16 is formed starting from the flat side 20, of the opening 14 of the groove 10 by a flat surface portion 21. This surface portion 21 is arranged at an angle β to the flat side 20. A curved portion 23 adjoins the surface portion 21. The above description of the contact surface 29 applies to the curvature of this surface portion 23. The curved portion 23 extends from an intersection point M to the apex K and is formed as an ascent. This means that the diameter of the groove 10 is reduced in the region of the surface portion 23, starting from the intersection point M to the apex K. The intersection point M is formed at the transition from the surface portion 21 to the surface portion 23. This intersection point M is arranged at a distance X from the flat side 20. After joining the two components 1 and 2, point A is arranged in a horizontal extension of the intersection point M on the contact surface 27 on the shaft 17 of component 1 and thus also at the same distance X from the flat side 20 of the second component. The two points, intersection point M and point A, are arranged spaced apart from one another. A further curved surface portion 30 can be arranged after the curved surface portion 23. The curved surface portions 23 and 30 can include values of the same or different sizes with regard to their degree of curvature and their length. The surface portion 23 is formed as an ascent; the surface portion 30 is formed as a descent. The above description for the ascent can also apply to the descent, with the difference that in the case of the descent, the diameter of the groove 10 increases from the apex K in the direction of the bottom 12. The ascent and the descent can also be shaped differently. The curved surface portions 23 and 30 and the apex K, which lies between these two surface portions 23 and 30, form the curvature, the contact surface 29. Following the curved surface portion 30, a further surface portion 22, which is the same or similar to the surface portion 21, can be arranged and formed. In the embodiment according to FIG. 3, the peripheral surface 16 of the groove 10 is formed by at least two surface portions; four (21, 23, 22, 30) surface portions are shown. The contact region 29 corresponds to the surface portions 23 and 30 between which the contact point KP is arranged. The surface portions 23, 30 each have a curvature that follows the above description. The proportion of the region of the surface portions 21, 23 and 30, 23 can, based on the peripheral surface 16, be of the same size or different sizes. A secure connection according to the invention is created when the proportion of the curved surface portions 23 and 30 is 50% of the surface 28, preferably 30%, particularly preferably 15%.

This embodiment is an example of the fact that the contact surface 29 forms only part of the peripheral surface 16. Only this region is decisive for the strength of the connection because the contact point KP is only in this region.

Figure 4:
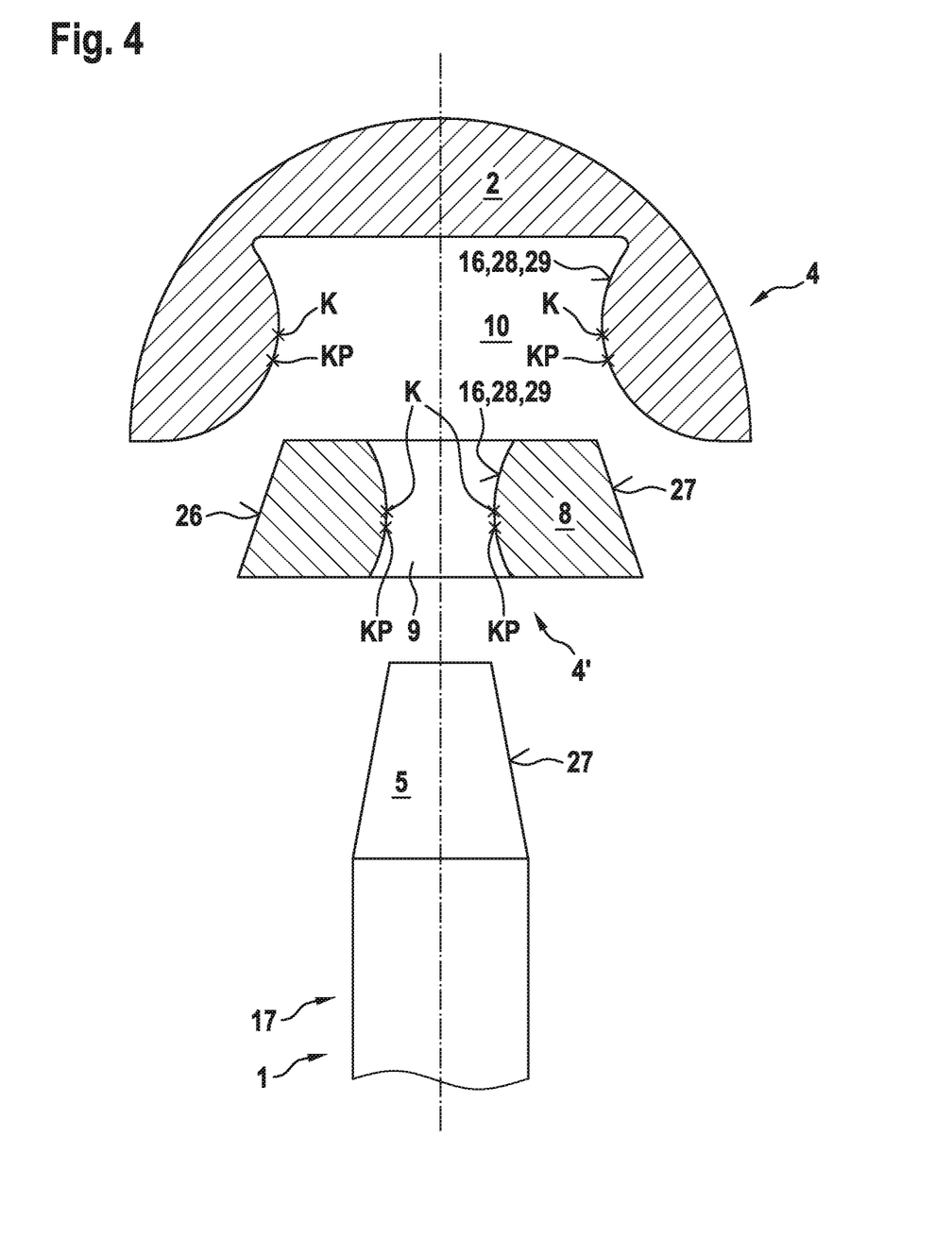
FIG. 4: is a cross section of an alternative form of a connection according to the invention of three components, in section and in a schematic representation.

FIG. 4 shows an orthopedic system consisting of a first component 1, a second component 2, and a third component 8, a connecting part, an adapter 8. The same reference numerals have the same meaning as described above. This orthopedic system has two connection arrangements 4 and 4' according to the invention. A first connection arrangement 4 is arranged between the second component 2 and the adapter 8, and a second connection arrangement 4' is arranged between the adapter 8 and the first component 1. The above description applies to the connection arrangement 4 between the second component 2 and the adapter 8.

The adapter 8 has a groove 9 in the shape of a through opening. The contact surface 29 on the peripheral surface 16, the surface 28 of the groove 9, is curved in accordance with the above description. The shaft 17 of the first component 1 is formed in accordance with the above description. An arrangement according to FIG. 4 can provide an orthopedic system made up of a plurality of components 1, 2, 8 having a plurality of connection arrangements 4, 4' according to the invention.

As an alternative to the arrangement of the curved contact surface 29 shown in FIG. 4, this can also be arranged on other surfaces, for example on the outer peripheral surface 26 of the adapter 8 or on the attachment 5 of the first component 1. Regardless of the arrangement of the curved contact surface 29, a connection arrangement 4, 4' according to the invention has a curved surface 16, 28, 29 arranged on one component and a contact surface 27 in operative connection thereto arranged on a second or third component. Both the curved surface 29 and the contact surface 27 can be partial regions of individual surfaces.

Figure 5:
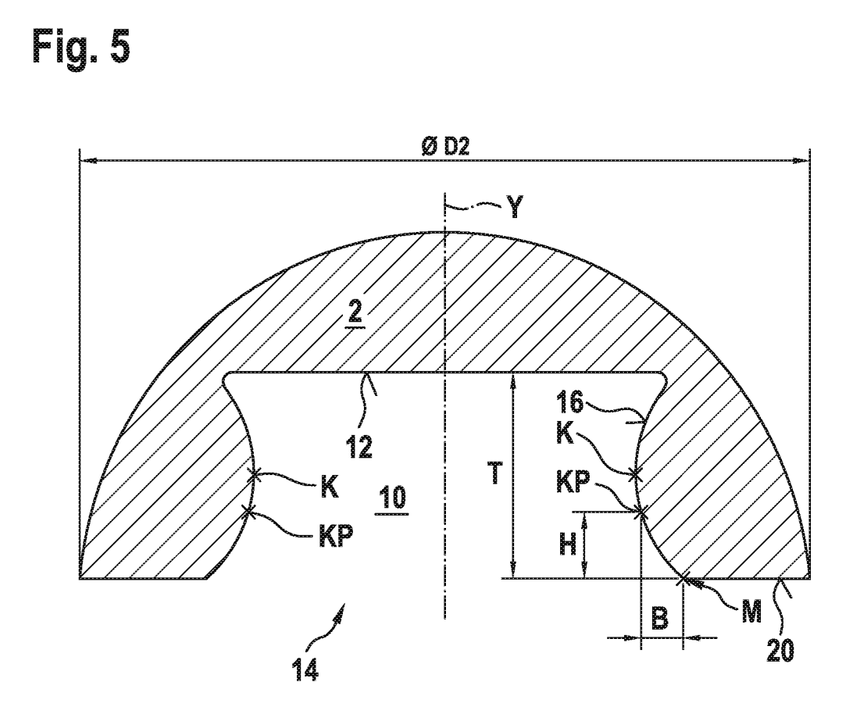
FIG. 5 shows the connection point enlarged according to FIG. 1, in section and in a schematic representation.

FIG. 5 shows an example of a component 2 of a ball head having a diameter D2 and the positioning of the contact point KP on the peripheral surface 16. The contact point KP is arranged at a distance H from the flat side 20. T is the depth of the groove 10 and extends from the bottom 12 of the groove 10 to the opening 14 to the flat side 20 of the component 2. The peripheral surface 16 of the groove 10 is curved as above. Starting from the intersection point M, which is arranged on the flat side 20 according to FIG. 5, the curvature extends in the direction of the central axis Y. As a result, the contact point KP is arranged offset in the direction of the central axis Y to the intersection point M. A distance B is formed between the contact point KP and the intersection point M. In the embodiment according to FIG. 5, the value corresponds to $H=T/3$. Depending on the applications, the contact point KP can be arranged om another location, but it is always arranged below the apex K.

A connection arrangement according to the invention of two components has on at least one of these components a curved surface portion having an apex K and a contact point KP. The curved surface portion can extend over the entire surface of a groove, for example. Then a closed azimuth is created from the apexes, a circumferential line which is formed from a plurality of contact points KP lined up in a row. After joining the two components, a linear operative connection is created at this apex or at this azimuth.

Figure 6:
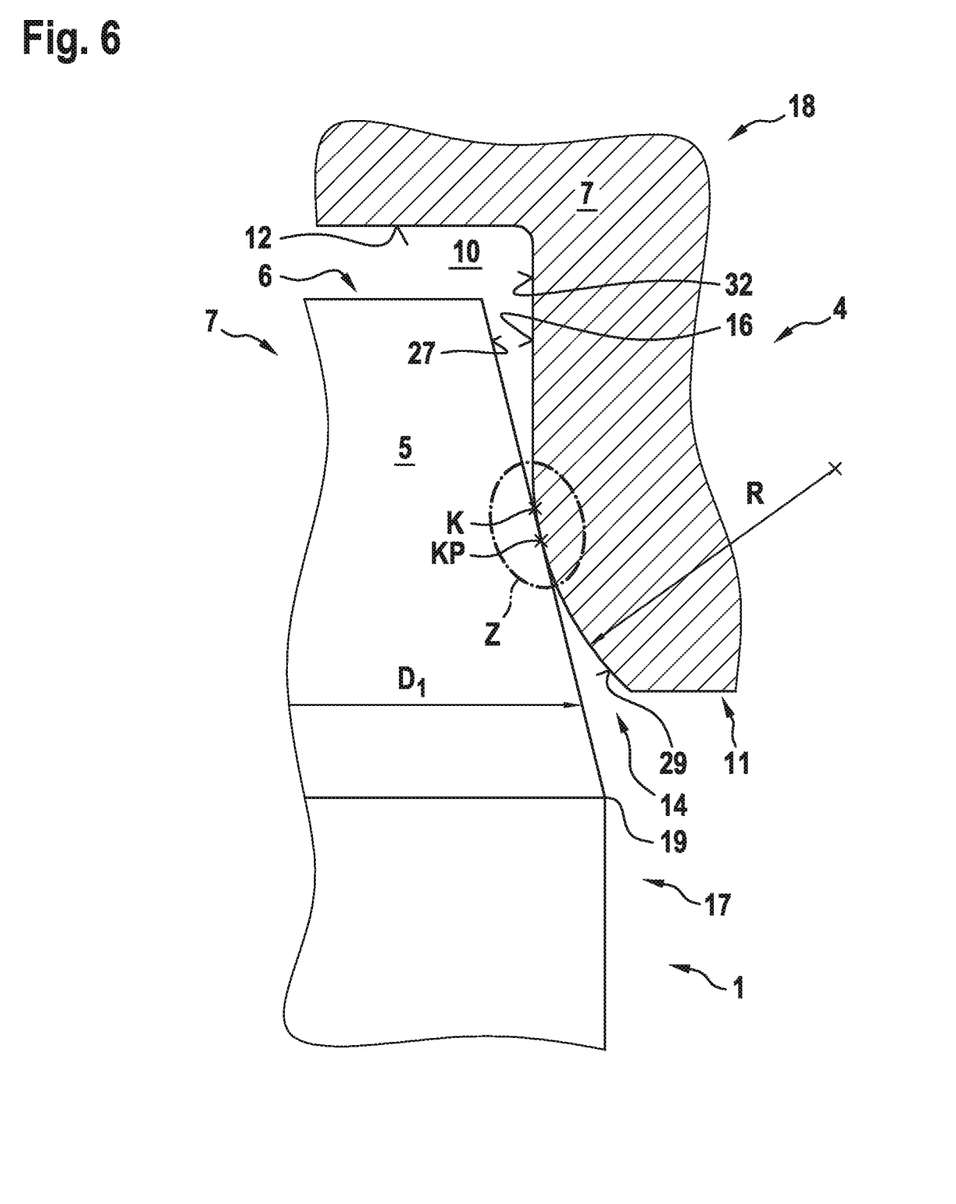
FIG. 6 is an alternative embodiment of the connection point in section and in a schematic representation.

FIG. 6 shows an alternative connection arrangement 4 of two orthopedic components, here a shaft 17 of a first component 1, having a ball head 18 of a second component 2. The shaft 17 has a projection or an attachment 5 at its first end 7. Starting from a location 19 of the shaft 17, the diameter D1 of the attachment 5 continuously decreases to its distal end 6 and forms a truncated cone. The truncated cone has a peripheral or contact surface 27. Like all other design variants, the two components can be part of a hip joint prosthesis, a shoulder joint prosthesis, or a finger or ankle prosthesis or other joint prostheses.

The second component 2 has a recess or groove 10. The groove 10 is delimited by a peripheral surface 16 and a base surface or a bottom 12 and opposite the bottom by an opening 14. In this embodiment, the peripheral surface 16 is made in two parts, i.e. it consists of two different geometric shapes. Starting from the second end 11 of component 2, from the opening 14 of the groove 10, the peripheral surface 16 of the groove 10 is curved and forms the contact surface 29 on which the contact point KP is located. The curvature of the contact surface 29 creates a convexly curved surface. Starting from the opening 14 of the groove 10, the amount of the diameter D1 of the groove 10 decreases to a point, the apex K. From this apex K, the amount of the diameter D1 to the bottom 12 remains constant, i.e. from this apex K the peripheral surface 16 forms a hollow cylinder 32. The cavity in the hollow cylinder 32 serves to receive the remaining part of the shaft 17, the part of the attachment 5 which is arranged between the contact point KP, and the distal end 6 of the shaft 17. Synovial fluid will be present in this region when implanted.

In this embodiment, the contact surface 29 is formed preferably circular.

When joining the shaft 17 of the first component 1 with the ball head 18 of the second component 2, the contact of the two components is created at the contact point KP. The contact point KP lies on the peripheral surface 16 or the contact surface 29 below the apex K in the direction of the second end 11 or the opening 14. The gap between the contact point KP and the apex K depends on the geometric configuration of the truncated cone of the first component 1 and the curvature of the contact surface 29 of the second component 2.

This embodiment has the decisive advantage that the precise location of the contact point KP can easily be determined by the circular design of the contact surface 29, inter alia from the taper angle of the projection 5 and the radius R. The formation of the cavity above the apex K as a hollow cylinder 32 considerably simplifies the production of component 2.

Figure 7:
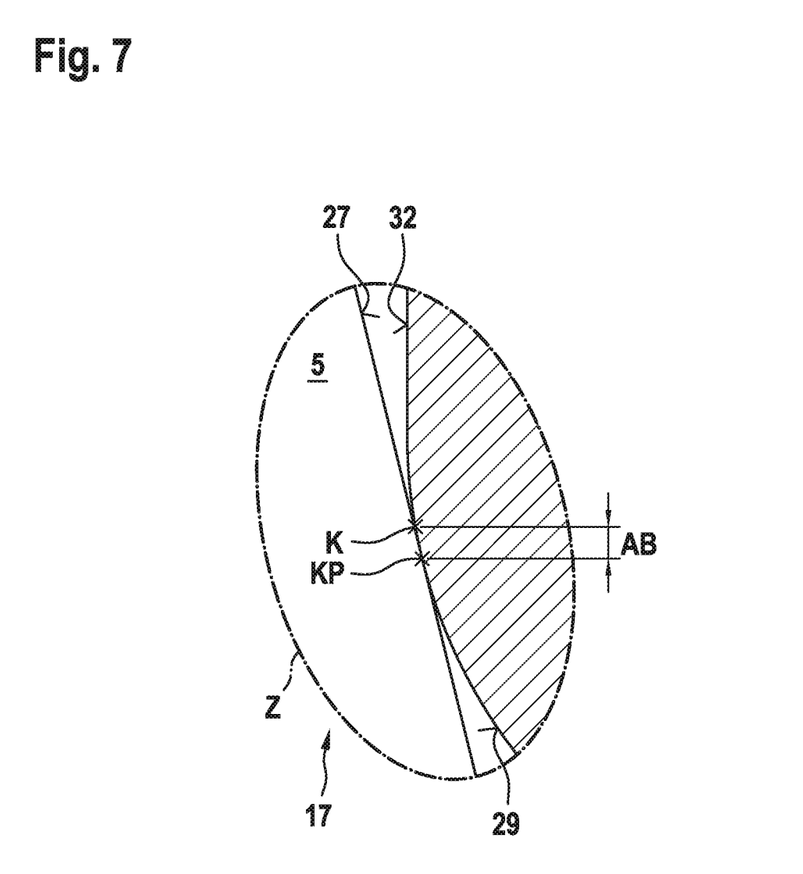
FIG. 7 is the section Z from FIG. 6 in an enlarged representation, not to scale to make it easier to see the essential.

FIG. 7 shows a section Z from FIG. 6. The circular contact surface 29 can be seen, on which the contact point KP is located and which merges into the hollow cylinder 32 at the apex K. At the contact point KP, the contact surface 29 touches the contact surface 27 of the projection 5 of the shaft 17.

FIG. 8 shows again schematically a connection arrangement 4 according to the invention having a second orthopedic component 2, namely a ball head and a first orthopedic component, namely a shaft 1, the upper end of which is formed as a taper. The peripheral surface 16 or the contact surface 29 of the ball head is formed as part of a ring having the radius R. A complete ring is shown for clarity. The longitudinal axis is identified by reference numeral 33. In this embodiment, the longitudinal axis 33 also forms the axis of rotation.

Figure 8:
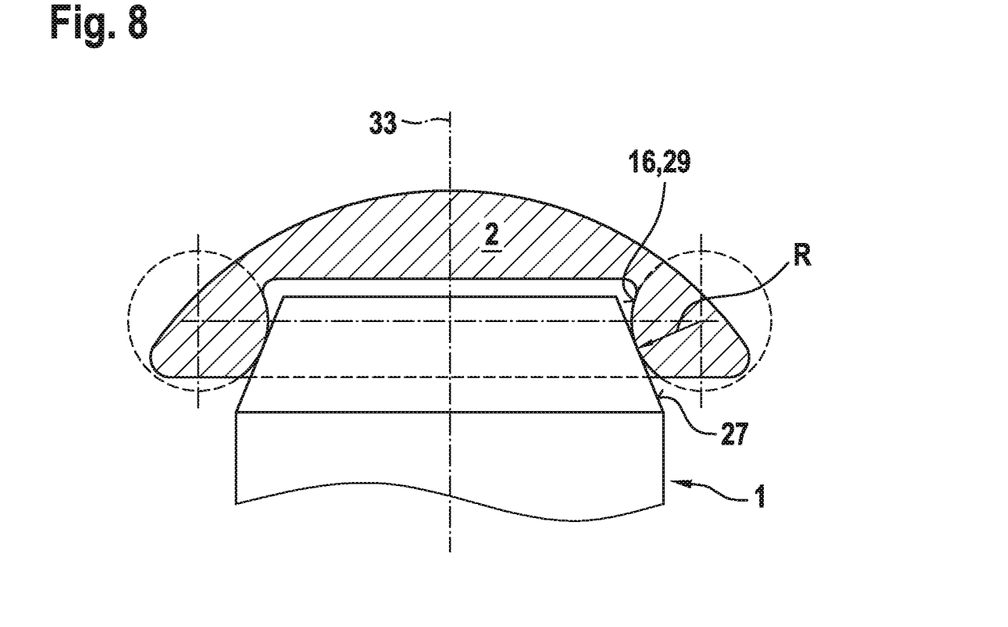
FIG. 8 is a cross section of an alternative form of a connection according to the invention having a large taper angle and thus a flat design.
Figure 9:
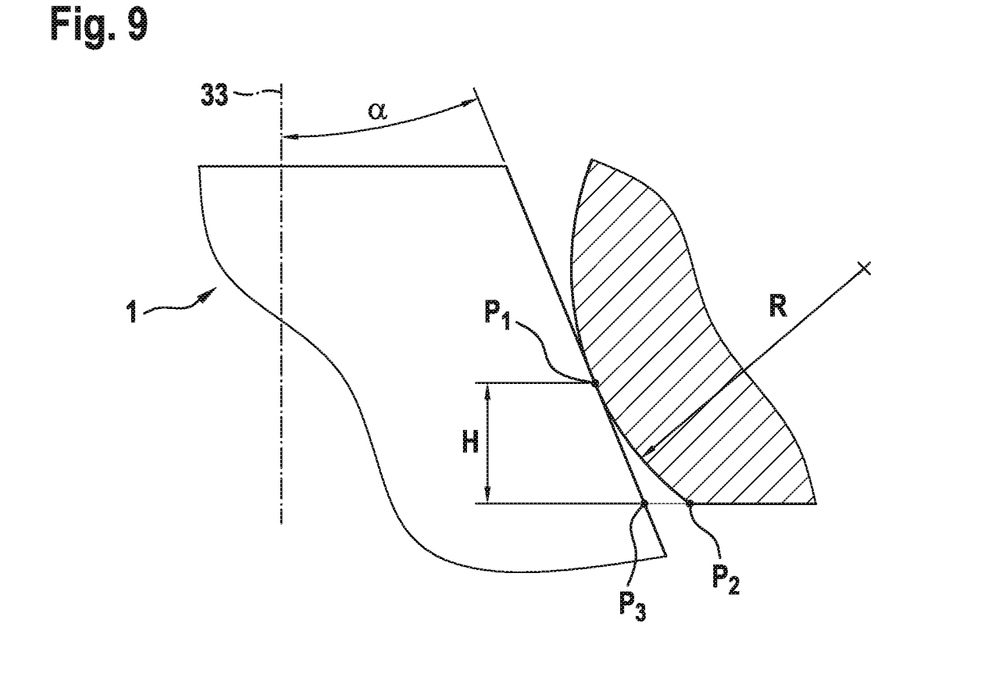
FIG. 9 shows the connection point according to FIG. 8 enlarged, in section and in a schematic representation.

FIG. 9 shows the connection point, i.e. a contact point KP enlarged according to FIG. 8, in section and in a schematic representation. At the contact point KP, here designated P1, the part of the first orthopedic component 1 designed as a taper touches the contact region 29 of the ball head formed as a ring having the radius R. The taper angle of the projection 5 is marked here with a and forms the "male taper." The distance P2-P3 denotes the gap at orifice. The contact point P1 is at a height H from the gap at orifice.

Figure 10:
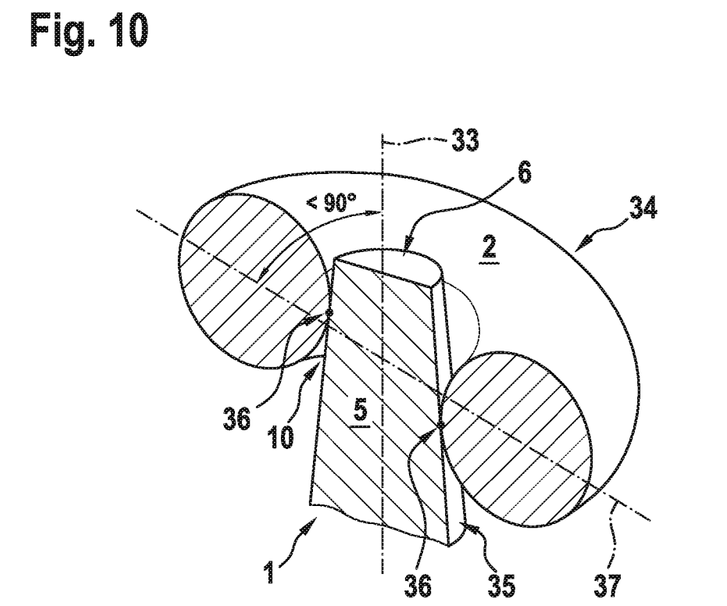
FIG. 10 shows an example of a 2-point contact between a taper and a ring.
Figure 11:
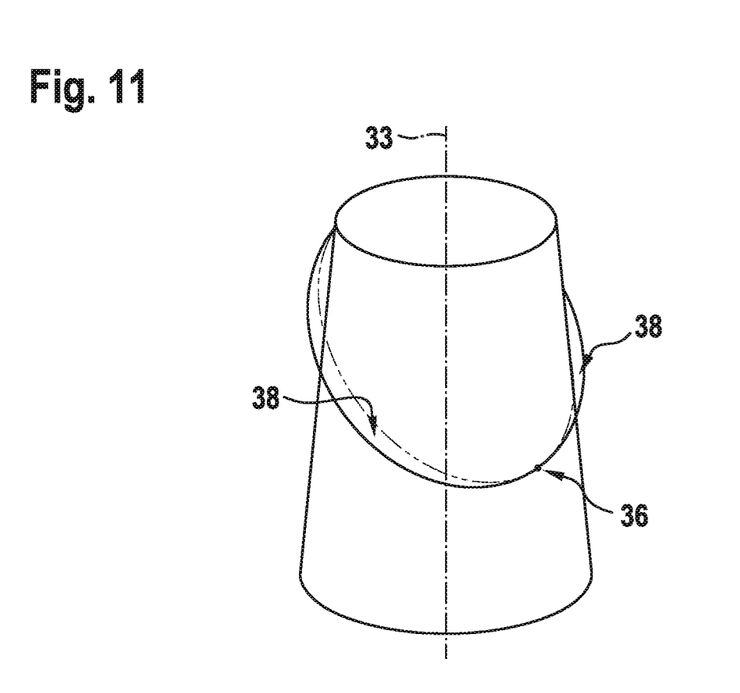
FIG. 11 shows the taper according to FIG. 10 having the drawn contact gap to the ring.

FIGS. 10 and 11 show in a 3D representation the joining process of two components 1, 2, which are initially arranged at an angle that deviates from an orthogonal alignment. The attachment 5 of a first component 1 is inserted into a groove 10 of a second component 2, wherein a 2-point contact is first created between the attachment 5, the taper 35 of a first component 1, and an annular contact surface 29 of a second component 2. This 2-point contact is created when two components (1 and 2) are arranged at an angle that deviates from 90° to one another. Reference numeral 33 shows the longitudinal axis of component 1; reference numeral 37 shows the longitudinal axis of component 2. These two axes are arranged at an angle that deviates from 90° to one another. This initially results in a 2-point contact. With the reference numeral 36, the contact points of a 2-point contact are designated (see FIG. 10).

FIG. 11 shows the taper 35 according to FIG. 10 and the contact surface 29 of the component 2. Components 1 and 2 are arranged at an angle to one another, deviating from 90°.

Thereby, a 2-contact point connection is created between components 1 and 2. One of the two contact points is shown and provided with the reference numeral 36. The second contact point is arranged at a distance of 180° from the first contact point. There is a gap 38 between the contact points, which increases starting from a contact point 36 in the direction of the second contact point 36. The gap 38 has its greatest width in the region of half the distance between the contact points.

The joining condition according to FIGS. 10 and 11 of two components is not stable and permanent and should be avoided. The arched surface according to the invention on at least one component transfers the connection when further joining from a 2-contact point connection to a line contact. Starting from the joining state according to FIG. 10, the attachment 5 of the first component 1 is inserted further into the groove 10 of the second component 2 for example. The arched contact surface 29 according to the invention transfers the 2-contact point connection to a line contact and at the same time to an orthogonal alignment of the two components 1 and 2. This makes it possible to convert the joining state according to FIGS. 10 and 11 into a joining state according to FIG. 1. In the embodiment according to FIG. 1, the two components 1 and 2 are arranged at a 90° angle to one another. Thereby, before the force is applied, a line contact is created that extends over the entire peripheral surface.

The invention claimed is:

1. A connection arrangement of an orthopedic system for connecting a plurality of components, the connection arrangement comprising:
    a first component having an outer contact surface formed as a taper; and
    a second component having a bore having an inner contact surface,
    wherein the inner contact surface includes a single convex part having a circular cross section such that, when assembling the first component and the second component before a force is introduced from a 2-contact point connection, a line connection is created between the outer contact surface of the first component and the single convex part of the inner contact surface of second component, and when the force is applied the line connection changes into a strip connection by plastic deformation, on the basis of which the first and second components hold together.

2. The connection arrangement according to claim 1, wherein the line connection and the strip connection are formed all around on the components.

3. The connection arrangement according to claim 1, wherein one of the outer and inner contact surfaces is made of metal and the other of the outer and inner contact surfaces is made of ceramic.

4. The connection arrangement according to claim 1, wherein the single convex part of the inner contact surface of the second component extends from a groove formed at a bottom of the bore, along a peripheral surface of the bore, and to an opening of the bore.

5. The connection arrangement according to claim 1, wherein the single convex part of the inner contact surface is continuously formed, wherein the function thereof can be continuously differentiated twice at any point.

6. The connection arrangement according to claim 1, wherein the outer contact surface of the first component is arranged on a projection of the first component.

7. An orthopedic system comprising at least two components having a connection arrangement according to claim 1.

8. An orthopedic system comprising at least two components having two connection arrangements according to claim 1.

\* \* \* \* \*